(12) United States Patent
Fabre et al.

(10) Patent No.: US 6,599,540 B1
(45) Date of Patent: Jul. 29, 2003

(54) **USE OF A *SERENOA REPENS* EXTRACT FOR THE PRODUCTION OF A MEDICAMENT TO TREAT PROSTATE CANCER**

(75) Inventors: Pierre Fabre, Castres (FR); Jean-Pierre Raynaud, Paris (FR); Henri Cousse, Pins Justaret (FR)

(73) Assignee: Pierre Fabre Medicament, Boulogne-Billancourt (FR)

( * ) Notice: Subject to any disclaimer, the term of this patent is extended or adjusted under 35 U.S.C. 154(b) by 0 days.

(21) Appl. No.: 09/937,676

(22) PCT Filed: Mar. 30, 2000

(86) PCT No.: PCT/FR00/00804
§ 371 (c)(1),
(2), (4) Date: Sep. 28, 2001

(87) PCT Pub. No.: WO00/57892
PCT Pub. Date: Oct. 5, 2000

(30) Foreign Application Priority Data

Mar. 30, 1999 (FR) .............................. 99 03959

(51) Int. Cl.[7] .............................................. A61K 35/78
(52) U.S. Cl. ..................................................... 424/727
(58) Field of Search ........................................ 424/727

(56) References Cited

U.S. PATENT DOCUMENTS

| | | | | |
|---|---|---|---|---|
| 5,665,393 A | * | 9/1997 | Chen et al. | 424/489 |
| 6,039,950 A | * | 3/2000 | Khwaja et al. | 424/727 |
| 6,197,309 B1 | * | 3/2001 | Wheeler | 424/727 |
| 6,200,573 B1 | * | 3/2001 | Locke | 514/254 |
| 6,261,607 B1 | * | 7/2001 | Newmark et al. | 424/727 |
| 6,399,115 B2 | * | 6/2002 | Revel | 424/727 |
| 6,482,447 B2 | * | 11/2002 | Revel | 424/727 |

FOREIGN PATENT DOCUMENTS

| | | | |
|---|---|---|---|
| FR | 2480754 | * | 10/1981 |
| WO | 9320832 | * | 10/1993 |

OTHER PUBLICATIONS

Kuritzky "Benign Prostatic Hyperplasia" COMP THER 24(3) 130–135 1998.*

Life Extension –Disease Prevention and Treatment "Prostate Cancer: Anticancer Properties and Activity of PC–SPES" ISBN 0–96587–7744 published Jan. 2000.*

DiPaola et al "Clinical and Biologic activity of an estrogenic herbal combination (PC–SPES) in Prostate Cancer" New Engl. Jour Med. vol. 12 p. 785–791 (1998).*

Meschino, James "Nutrition and Men's Health" Treating Prostate Enlargement with Saw PALMETTO http://www.renaisante.com./html/nutrition_men_s_health (1998).*

Meschino, James "A Review of Prostate Nutritional Support" http://www.renaisante.com/html/nutrition_men_s_health (2000).*

Ravenna L., et al. Effects of the Lipidosterolic Extract of *Serenoa repens* (Perimixon®) on Human Prostatic Cell Lines. The Prostate 1996;29:219–230.

Délos S., et al. Inhibition of the Activity of 'Basic' 5α–Reductase (Type I) Detected in DU 145 Cells and Expressed in Insect Cells. J. Steroid Biochem. Molec. Biol., 1994; 48(4):347–352.

Bayne C.W., et al. *Serenoa repens* (Permixon®): A 5α–Reductase Types I and II Inhibitor—New Evidence in a Coculture Model of BPH. The Prostate 1999;40:232–241.

Bayne C.W., et al. The Selectivity and Specificity of the Actions of the Lipido–Sterolic Extract of *Serenoa repens* (Permixon®) on the Prostate. J. Urol. 2000;164:876–881.

Paubert–Braquet M., et al. Effects of the lipidosterolic Extract of *Serenoa repens* (LSESr®) and its Major Components on Basic Fibroblast Growth Factor Induced Proliferation of Cultures of Human Prostate Biopsies. Eur. Urol. 1998;33:340–347.

Chevalier, G., et al. Distribution Study of Radioactivity in Rats After Oral Administration of the Lipido/Sterolic Extract of *Serenoa repens* (Permixon®) Supplemented with $[1^{14}C]$–Oleic Acid or $[4–^{14}C]$–β–Sitosterol. Eur. J. Drug Metab. Pharmacokinet. 1997;1:73–83.

Paubert–Braquet M., et al., Effect of *Serenoa repens* Extract (Permixon®) On Estradiol/Testosterone–Induced Experimental Prostate Enlargement in the Rat. Pharmacological Research 196;34:171–179.

Plosker G.L., et al. *Seronoa repens* (Permixon®) A Review of its Pharmacology and Therapeutic Efficacy in Benign Prostatic Hyperplasia. Drugs and Aging 1996; Nov. 9(5):381–395.

Carraro J., et al. Comparison of Phytotherapy (Permixon®) with Finasteride in the Treatment of Benign Prostate Hyperplasia: A Randomized International Study of 1,098 Patients. The Prostate 1996;29:231–240.

DiSilverio F., et al. Effects of Long–Term Treatment with *Serenoa repens* (Permixon®) on the Concentrations and Regional Distribution of Andorgens and Epidermal Growth Factor in Benign Prostatic Hyperplasia. The Prostate 1998;37:77–83.

Vacherot F., et al. Induction of Apoptosis and Inhibition of Cell Proliferation by the Lipido–Sterolic Extract of *Serenoa repens* (LSESr, Permixon®) in Benign Prostatic Hyperplasia. The Prostate 2000; 45:259–266.

* cited by examiner

*Primary Examiner*—Herbert J. Lilling
(74) *Attorney, Agent, or Firm*—The Firm of Hueschen and Sage

(57) ABSTRACT

The invention relates to the use of a lipido-sterolic *Serenoa repens* extract for the production of a medicament which is administered in an isolated manner or in an associated manner, in a simultaneous, separated or staggered manner, with prostatectomy, radiotherapy and/or hormonotherapy in order to prevent and/or treat prostate cancer.

6 Claims, No Drawings

USE OF A *SERENOA REPENS* EXTRACT FOR THE PRODUCTION OF A MEDICAMENT TO TREAT PROSTATE CANCER

The present invention relates to the field of treating prostate cancer which, at the present time, is based on several therapeutic routes dependent on the degree of progress of the disease. The hormonal treatment of metastatic prostate cancer which has crossed the capsule currently relies mainly on several categories of medicinal products which act at different levels on the hypothalamo-gonad axis.

The efficacy and limits of hormonal treatments are now more or less defined. These limits are set both by the side effects, in particular vascular effects for estrogens at high doses, and sexual, gastric and pulmonary effects for antiandrogens, and by the emergence of immediate or secondary resistance.

The current attitude appears to be focused, at least at the initial phase of the treatment, on total androgenic blockage (inhibition of the testicular secretion of androgens and inhibition of the activity of the residual androgens on the target organ). Specifically, the absence of absolute certainty regarding the advantage of continuing this combination long term occasionally results in a complete androgenic blockage being preferred at the time of starting a treatment with an LHRH agonist, in order to prevent initial flare-ups with subsequent continuation of the agonist alone.

The prognosis for developed prostate cancers and the androgen dependence of many of them is encouragement for eradicating as fully as possible the androgenic environment, including the adrenal environment. The superiority of a long-term combined treatment (surgical castration or LHRH agonist combined with an antiandrogen therapy) on the life expectancy is more and more confirmed.

Irrespective of the initial hormonal treatment applied, the response barely goes beyond two years up to the installation of the hormone resistance phase. Neither a change in hormone therapy nor the use of chemotherapy has hitherto made it possible to prolong significantly the median survival time, which remains about eighteen months.

Hormone therapy, with the aim of eliminating the hormones responsible for the tumor growth, generally involves the administration of LHRH agonists alone or combined with antiandrogen agents (see for example patent FR 2 465 486).

Cancerous prostate cells may also be partially eliminated by radiotherapy and/or by surgical intervention.

For the treatment of prostate cancer, a practitioner therefore currently has several means of intervention at his disposal. Mention will be made firstly of surgery, then of LHRH analogs, and finally of antiandrogens used either in combination with medical or surgical castration or in monotherapy, and finally radiotherapy.

However, none of these means is considered entirely satisfactory at the present time. Although it is known that hormone sensitivity justifies the use of hormone therapy, the studies conducted to date do not enable the optimum modes of the benefit/risk ratio to be defined precisely.

Specifically, chemical castration leads to impotence and a reduction in libido, this effect possibly being reversible on stopping the treatment, but with a risk of more or less long-term relapse.

The present invention constitutes a decisive improvement in the treatment of prostate cancer. The invention is directed more particularly toward the use of a lipid-sterol extract of *Serenoa repens* to manufacture a medicinal product to be administered individually or in combination, simultaneously, separately or sequentially over time, with a prostatectomy, radiotherapy and/or a hormone therapy, for the treatment or prevention of prostate cancer.

In the context of the present invention, it has been observed that the lipid-sterol extract of *Serenoa Repens* plays a role in inducing apoptosis, allowing the first line treatment before surgery or radiotherapy, in order to avoid the dissemination of the tumor outside the prostate capsule.

In addition, the lipid-sterol extract of *Serenoa Repens* combined with a hormonal treatment makes it possible, on stopping the hormonal treatment, to control the tumor progression by inducing cell death. Such a sequential treatment enables the benefit/risk ratio to be improved considerably.

Finally, after prostatectomy and/or after radiotherapy, the lipid-sterol extract of *Serenoa* Repens retards the progression of cancer cells which might have escaped treatment.

To illustrate the hormone therapy treatment combined with the administration of the lipid-sterol extract of *Serenoa Repens* according to the invention, mention will be made firstly of LHRH agonists or antagonists, in particular triptorelin, leuprorelin, nafarelin, goserelinor or buserelin and also nonsteroidal antiandrogens such as flutamide, nilutamide or bicalutamide.

According to one advantageous variant of the present invention, said medicinal product is administered in combination with an antiandrogen combined with an LHRH agonist or antagonist.

The lipid-sterol extract of *Serenoa Repens* has been used hitherto for treating benign hyperplasia of the prostate. In the context of the present invention, it has been found, unexpectedly, that the lipid-sterol extract of *Serenoa Repens* can in fact act as an apoptosis inducer for prostate epithelial and stromal cells.

Following these observations, several clinical trials were conducted, which have made it possible to site the advantage of the lipid-sterol extract of *Serenoa Repens* among the therapeutic arsenal used for treating prostate cancer.

It should be recalled that the lipid-sterol extract of *Serenoa Repens* is an assayed extract obtained from *Serenoa Repens* (Sabal Serrulata, Saw Palmeto).

This extract is obtained more particularly using hydrophobic solvents such as supercritical $CO_2$ or hexane. Such an extract contains no phytoestrogens, which differentiates it from soya isoflavones or from any other phytoestrogens as described, for example, in New England J. of Medicine Vol. 339 (12) pp. 785–791.

This extract may be assayed as free fatty acids (lauric acid+oleic acid=65%) and as fatty alcohols which are traces of the unsaponifiable portion (0.2%). For a more complete description of the process for manufacturing such an extract, reference may be made, for example, to the description of patent FR 2 480 754.

As nonlimiting examples, the invention will be illustrated by the three positive clinical trials whose protocols are given below.

1st Study:

The lipid-sterol extract of *Serenoa Repens* was used at a dose of 320 mg administered three times a day.

The patients are men of 50 to 75 years old, with a localized prostate cancer (stage T1C, T2A and T2B) detected by positive biopsy.

This study showed in the groups treated with the lipid-sterol extract of *Serenoa Repens* a significant increase in cell death compared with an untreated group (awaiting surgery).

Compared with patient s treated with LHRH and antiandrogen during this same three-month period, the effect on apoptosis was similar (significant increase in the apoptotic index), but in the groups treated with the lipid-sterol extract of *Serenoa Repens,* the quality of life was maintained, more particularly as regards sexuality (evaluated by a suitable questionnaire and validated).

2nd Study:

The lipid-sterol extract of *Serenoa Repens* was administered at a daily dose of 960 mg for six months to patients after stopping a three-month hormonal treatment.

A control group received no replacement treatment and, after six months, a significant difference was obtained on the rate of biological escape, which demonstrates an advantage of the lipid-sterol extract of *Serenoa Repens* for a sequential treatment.

Given these results, a long-term study was undertaken over five years, the protocol of which is given below.

3rd Study:

After radiotherapy or radical prostatectomy, in certain patients, due to the difficulty of surgical intervention associated with the difficulty of access, a complementary treatment is required to control the development of the cells not removed. In general, after surgery, a waiting period without treatment is observed, during which the harmlessness of the lipid-sterol extract of *Serenoa repens* was exploited to be administered for five years at a dose of 640 mg/day.

The results of this study are compared in terms of benefit (risk of escape and relapse) with patients who have received no treatment.

Every year, a control is carried out, and, if need be, a hormonal treatment is replaced.

These clinical studies illustrate the therapeutic positioning of the lipid-sterol extract of *Serenoa repens* as an apoptosis inducer in neoadjuvant treatments.

Finally, it will be pointed out that the lipid-sterol extract of *Serenoa Repens* may be used in the context of the present invention in various forms of pharmaceutical preparations. These may be in particular gel capsules or wafer capsules.

The lipid-sterol extract of *Serenoa Repens* consequently constitutes an apoptosis inducer which may be used either as a firstline treatment for preventing or treating a newly established cancer, or as sequential hormone therapy treatments.

The invention also covers the use of the lipid-sterol extract of *Serenoa Repens* for the manufacture of a medicinal product to be administered in the context of a treatment combined in particular with hormone therapy. The clinical studies have documented the satisfactory tolerance and the efficacy of this inducer which may be used alone, but whose effects complementary to the hormonal treatments markedly improve the therapeutic management.

The lipid-sterol extract of *Serenoa Repens* thus constitutes a neoadjuvant which may be used in the treatment of prostate cancer at all the stages of development of the disease, alone or combined with other existing treatments and more particularly with treatments involving LHRH agonists or antagonists.

What is claimed is:

1. A method of treating a living human body afflicted with prostate cancer by administering a lipid-sterol extract of *Serenoa Repens* alone or in combination, simultaneously, separately or sequentially over time, with a prostatectomy, radiotherapy and/or a hormone therapy, for reduction of risk to develop prostate cancer and or treatment of prostate cancer.

2. The method of claim 1, wherein the extract is to be administered in combination with an LHRH agonist or antagonist.

3. The method of claim 1, wherein the extract is administered in combination with a nonsteroidal antiandrogen.

4. The method of claim 1, wherein the extract is administered in combination with an antiandrogen combined with an LHRH agonist or antagonist.

5. The method of claim 2, wherein the LHRH agonist or antagonist is selected from triptorelin, leuporelin, nafarelin, goserelin or buserelin.

6. The method of claim 3, wherein the nonsteroidal antiandrogen is selected from flutamide, nilutamide and/or bicalutamide.

* * * * *

UNITED STATES PATENT AND TRADEMARK OFFICE
CERTIFICATE OF CORRECTION

PATENT NO.   : 6,599,540 B1
DATED        : July 29, 2003
INVENTOR(S)  : Pierre Fabre et al.

It is certified that error appears in the above-identified patent and that said Letters Patent is hereby corrected as shown below:

<u>Column 2,</u>
Line 22, "goserelinor" should be -- goserelin --.
Line 66, "patient s" should be -- patients --.

<u>Column 4,</u>
Line 34, "leuporelin" should be -- leuprorelin --.

Signed and Sealed this

Eleventh Day of November, 2003

JAMES E. ROGAN
*Director of the United States Patent and Trademark Office*